(12) United States Patent
Kent (10) Patent No.: US 11,565,112 B2
(45) Date of Patent: Jan. 31, 2023

(54) ACTIVE TITRATION OF ONE OR MORE NERVE STIMULATORS TO TREAT OBSTRUCTIVE SLEEP APNEA

(71) Applicant: Vanderbilt University, Nashville, TN (US)

(72) Inventor: David T. Kent, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 266 days.

(21) Appl. No.: 16/528,940

(22) Filed: Aug. 1, 2019

(65) Prior Publication Data
US 2020/0069947 A1 Mar. 5, 2020

Related U.S. Application Data

(60) Provisional application No. 62/727,184, filed on Sep. 5, 2018.

(51) Int. Cl.
*A61N 1/36* (2006.01)
*A61N 1/05* (2006.01)
(Continued)

(52) U.S. Cl.
CPC .......... *A61N 1/36078* (2013.01); *A61B 5/037* (2013.01); *A61B 5/087* (2013.01); *A61B 5/0809* (2013.01); *A61B 5/318* (2021.01); *A61B 5/369* (2021.01); *A61B 5/389* (2021.01); *A61B 5/398* (2021.01); *A61B 5/7267* (2013.01); *A61N 1/0529* (2013.01); *A61N 1/0551* (2013.01);
(Continued)

(58) Field of Classification Search
CPC .............. A61N 1/36078; A61N 1/0551; A61N 1/36139; A61N 1/0529; A61N 1/3611; A61B 5/318; A61B 5/369; A61B 5/389; A61B 5/398; A61B 1/37223; A61B 5/037; A61B 5/0809; A61B 5/087; A61B 5/7267; A61B 5/4836; A61B 5/4818
See application file for complete search history.

(56) References Cited

U.S. PATENT DOCUMENTS

2008/0154330 A1* 6/2008 Tehrani ................ A61N 1/3601
607/42
2010/0094376 A1* 4/2010 Penner ................ A61N 1/0517
607/42

(Continued)

*Primary Examiner* — Gary Jackson
*Assistant Examiner* — Sebastian X Lukjan
(74) *Attorney, Agent, or Firm* — Tarolli, Sundheim, Covell & Tummino LLP (57) ABSTRACT

The present disclose generally relates to systems and methods for active titration of one or more cranial or peripheral nerve stimulators to treat obstructive sleep apnea. The active titration can be accomplished in an automated fashion by a closed-loop process. The closed-loop process can be executed by a computing device that includes a non-transitory memory storing instructions and a processor to execute the instructions to perform operations. The operations can include defining initial parameters for the one or more cranial or peripheral nerve stimulators for a patient; receiving sensor data from sensors associated with the patient based on a stimulation with the one or more cranial or peripheral stimulators programmed according to the initial parameters; and adjusting the initial parameters based on the sensor data.

22 Claims, 5 Drawing Sheets

(51) Int. Cl.
*A61N 1/372* (2006.01)
*A61B 5/03* (2006.01)
*A61B 5/08* (2006.01)
*A61B 5/087* (2006.01)
*A61B 5/00* (2006.01)
*A61B 5/318* (2021.01)
*A61B 5/369* (2021.01)
*A61B 5/389* (2021.01)
*A61B 5/398* (2021.01)

(52) U.S. Cl.
CPC ..... *A61N 1/36139* (2013.01); *A61N 1/37223* (2013.01)

(56) References Cited

U.S. PATENT DOCUMENTS

| | | | | |
|---|---|---|---|---|
| 2010/0241195 | A1* | 9/2010 | Meadows | A61N 1/3611 607/62 |
| 2011/0295335 | A1* | 12/2011 | Sharma | A61N 1/3606 607/40 |
| 2013/0197321 | A1* | 8/2013 | Wilson | A61N 1/3601 600/301 |
| 2013/0296662 | A1* | 11/2013 | Omari | A61B 5/7282 600/301 |
| 2014/0228905 | A1* | 8/2014 | Bolea | A61F 5/56 607/42 |
| 2018/0015282 | A1* | 1/2018 | Waner | A61N 1/37217 |

* cited by examiner

FIG. 5

ACTIVE TITRATION OF ONE OR MORE NERVE STIMULATORS TO TREAT OBSTRUCTIVE SLEEP APNEA

CROSS-REFERENCE TO RELATED APPLICATIONS

This application claims the benefit of U.S. Provisional Application No. 62/727,184, entitled "Active Titration of a Cranial Nerve Stimulator to Treat Obstructive Sleep Apnea," filed Sep. 5, 2018. The entirety of this provisional application is hereby incorporated by reference for all purposes.

TECHNICAL FIELD

The present disclosure relates generally to treating obstructive sleep apnea and, more specifically, to systems and methods for active titration of one or more nerve stimulators to treat obstructive sleep apnea.

BACKGROUND

Sleep apnea is a sleep disorder in which breathing repeatedly stops and starts during sleep, leading to daytime sleepiness, as well as cardiac and neural complications. The most common type of sleep apnea is obstructive sleep apnea (OSA), affecting 29 million patients in the United States alone. OSA is characterized by recurrent airway obstructions, caused by the collapse of soft tissue structures surrounding the upper airway into the airway when the throat and tongue muscles relax during sleep. These airway obstructions are dangerous, leading to pauses in breathing or instances of shallow or infrequent breathing, negatively impacting a sufferer's health and quality of life.

While no FDA-approved drug therapies currently exist to treat OSA, several mechanical therapies exist, such as continuous positive airway pressure (CPAP) therapy or mandibular advancement device (MAD) treatment. These mechanical devices suffer from resistance to use and inconsistent treatment. The FDA has recently approved the first implantable cranial nerve stimulator for the treatment of OSA. The cranial nerve stimulator functions by stimulating the hypoglossal nerve, causing tongue stiffening and protrusion to prevent obstruction of the airway. Configuration of these devices requires manual titration based on a polysomnography study during an overnight stay at a sleep laboratory. In other words, the technician monitors the polysomnography data and makes adjustments to therapy on-the-fly as airway collapse is observed via flow limitation observed from respiratory airflow data and other biologic sensors. However, this method of titration is, by its very nature, often inexact, leading to subtherapeutic levels that allow airway collapse to continue or supratherapeutic levels that lead to uncomfortable stimulation that may arouse the patient from sleep.

SUMMARY

The present disclosure relates to systems and methods for active titration of one or more nerve stimulators to treat obstructive sleep apnea. The nerve stimulator can be a cranial or peripheral nerve stimulator that delivers a stimulation that affects the form or function of the upper airway directly or indirectly through connected structures (e.g., a hypoglossal nerve stimulator (HNS), a palatoglossal stimulator, a palatopharyngeus stimulator, a phrenic nerve stimulator, a stimulator of an ansa cervicalis, or the like) that can be used to treat obstructive sleep apnea. The titration is accomplished by a closed-loop computer system utilizing data from pharyngeal and/or esophageal manometry sensors and/or live data from polysomnography sensors to increase or decrease therapy strength.

In an aspect, the present disclosure can include a system that actively titrates one or more nerve stimulators for treating obstructive sleep apnea. The active titration of a single nerve stimulator by the system is shown, which can be extrapolated into actively titrating two or more nerve stimulators in concert. The system can include a non-transitory memory storing instructions; and a processor to execute the instructions to perform operations. The operations include defining initial parameters for a nerve stimulator for a patient; receiving sensor data from sensors associated with the patient based on a stimulation with the nerve stimulator programmed according to the initial parameters; and adjusting the initial parameters based on the sensor data.

In another aspect, the present disclosure can include a method for actively titrating one or more nerve stimulators for treating OSA. The active titration of a single nerve stimulator by the method is shown, which can be extrapolated into actively titrating two or more nerve stimulators in concert. Steps of the method can be stored in a non-transitory memory and executed by a processor. The steps can include defining initial parameters for a nerve stimulator for a patient; receiving sensor data from sensors associated with the patient based on a stimulation with the nerve stimulator programmed according to the initial parameters; and adjusting the initial parameters based on the sensor data.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "obstructive sleep apnea ("OSA")" can refer to a sleep disorder that is caused by complete or partial obstruction of a patient's airway, leading to repetitive episodes of shallow or paused breathing during sleep, despite the patient's effort to breathe. OSA can be caused by upper airway collapse during sleep.

As used herein, the term "upper airway collapse" can refer to the mechanical caving in of one or more pharyngeal structures (e.g., velum, tongue base, lateral walls, epiglottis, etc.).

As used herein, the terms "nerve stimulator" and "cranial or peripheral nerve stimulator" can be used interchangeably to refer to an implanted or external device that applies electrical stimulation to a cranial or peripheral nerve that emerges directly from the brain or the cervical spine (e.g. an ansa cervicalis, a loop of nerves that are part of the cervical plexus lying superficial to the internal jugular vein in the carotid triangle). One example of a cranial nerve stimulator is a "hypoglossal nerve stimulator" (HNS) that can stimulate the twelfth cranial nerve, which innervates muscles of the tongue, to control movement of the tongue. An example of a peripheral nerve stimulator is one that can stimulate a portion or totality of the ansa cervicalis, activating the suprahyoid and/or infrahyoid strap muscles. Other examples of cranial or peripheral nerve stimulators include, but are not limited to, a palatoglossal stimulator, a palatopharyngeus stimulator, a phrenic nerve stimulator, or the like.

As used herein, the terms "implantable" can refer to something that can be surgically inserted within a patient's body (e.g., under the skin of the patient).

As used herein, the term "titration" can refer to a continuous measure of a property of a patient and manual adjustment of a parameter (e.g., related to a medical device) related to the property.

As used herein, the term "sleep laboratory" can refer to a specialized center that monitors a patient's sleep patterns and conducts diagnostic studies, such as polysomnography.

As used herein, the term "polysomnography" can refer to an overnight sleep study to diagnose sleep disorders, such as obstructive sleep apnea. Numerous tests can be used in connection with polysomnography, including electroencephalogram, electrooculography, electromyogram, electrocardiogram, respiratory inductance plethysmography, nasal airflow, or the like.

As used herein, the term "subtherapeutic" can refer to a level of therapy below that required to see an optimal therapeutic effect.

As used herein, the term "supratherapeutic" can refer to a level of therapy above that required to see an optimal therapeutic effect.

As used herein, the term "manometry" can refer to a technique for measuring changes in the pressure at different locations resulting from a biological action. The biological action can be related to the esophagus (esophageal manometry) and/or the pharynx (pharyngeal manometry).

As used herein, the term "automated" can refer to a process that operates by machines or computers in order to reduce the amount of work done by humans.

As used herein, the term "machine-learning" can refer to one or more statistical techniques (or algorithms) to progressively improve performance on a specific task without being explicitly programmed. Example machine learning algorithms can include: Decision tree learning, Association rule learning, Artificial neural networks, Deep learning, Inductive logic programming, Support vector machines, Clustering, Bayesian networks, Reinforcement learning, Representation learning, Similarity and metric learning, Sparse dictionary learning, Genetic algorithms, Rule-based machine learning, Learning classifier systems, Feature selection, or the like.

As used herein, the term "active titration" can refer to an adjustment to a state or characteristic of a device (e.g., a cranial or peripheral nerve stimulator) that is done automatically in response to input and/or feedback (e.g., data related to airway collapse).

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "medical professional" can refer to an individual who provides care to a patient. A medical professional can be, for example, a doctor, a physician's assistant, a student, a nurse, a caregiver, a technician, or the like.

II. Overview

The present disclosure relates generally to titrating one or more cranial or peripheral nerve stimulators that can be used to treat obstructive sleep apnea. Upon implantation, the one or more nerve stimulators must be titrated to deliver the proper stimulation of the cranial and/or peripheral nerves. Previously, titration has been accomplished manually by a medical professional during an overnight visit to a sleep laboratory, based on polysomnographic data. However, this manual process is inexact, and can lead to subtherapeutic therapy with continued airway collapse or supratherapeutic therapy causing uncomfortable stimulations that arouse the patient from sleep. Accordingly, the present disclosure relates, more specifically, to systems and methods for active titration of nerve stimulator to treat obstructive sleep apnea.

The active titration uses a closed-loop computer system, which can be automated via a preprogrammed titration algorithm, which can employ a trained machine-learning approach (e.g., a neural network). The closed-loop system can receive input from a variety of sensors, such as those used in polysomnography and/or those used in esophageal and/or pharyngeal manometry. As a collapse occurs, indicated by the sensors, the closed-loop system can transmit new parameters for stimulation (in real time at the time of the collapse occurring) to the one or more nerve stimulators. Further adjustments to the new parameters can be made based on additional inputs from the variety of sensors based on the stimulation with the new parameters.

III. Systems

Figure 1:
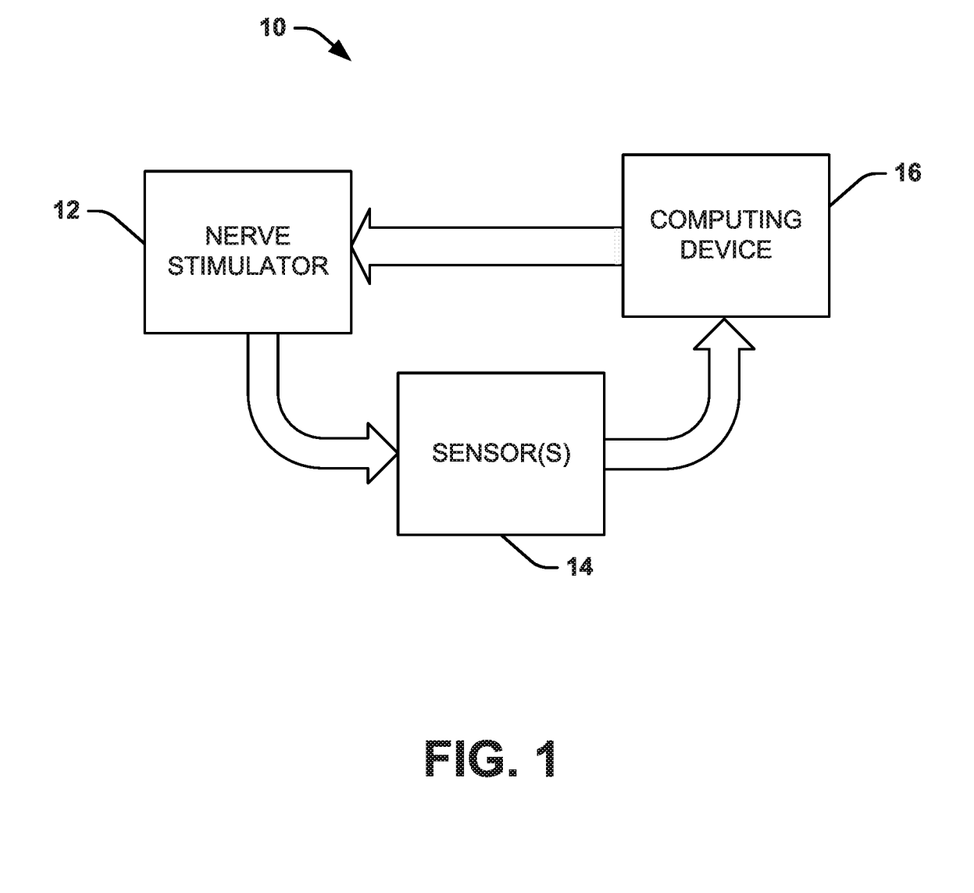
FIG. 1 is a schematic diagram showing a closed loop system to adjust parameters of one or more nerve stimulators in accordance with an aspect of the present disclosure.

One aspect of the present disclosure can include a closed loop system 10 that can be used to adjust parameters of one or more nerve stimulators in real time as a collapse is occurring. In FIG. 1, a single nerve stimulator 12 (e.g., a cranial or peripheral nerve stimulator) is illustrated and will be described, but it will be understood that multiple nerve stimulators can be configured with adjusted parameters in concert according to the system 10. In some instances, the nerve stimulator 12 can be a hypoglossal nerve stimulator (HNS) and/or a stimulator of an ansa cervicalis that can be used to treat obstructive sleep apnea (OSA). In traditional adjustment procedures, a patient stays overnight in a sleep lab, where a medical professional observes sensor outputs and manually adjusts the stimulator based on flow data. In contrast, the closed loop system 10 provides an automated solution implemented by a computing device 16 that can adjust parameters of the nerve stimulator 12 on the fly based on output from sensors 14 that is input to the computing device 16. The automated solution can be more precise than the traditional medical professional and able to set parameters for one or more nerve stimulators. Additionally, the parameters can be optimized for the patient, and not just adequate for the patient.

The closed loop system 10 includes at least the nerve stimulator 12, one or more sensors 14, and the computing device 16. The computing device 16 can transmit one or more initial parameters to the nerve stimulator 12. The transmission can be via a wireless connection. In some instances, the wireless transmission can be a short range wireless transmission, such as a Bluetooth transmission, a Bluetooth Low Energy transmission, or the like. The initial parameters can be chosen based on pre-procedural testing of the patient or using parameters previously known to be tolerable to the patient or one or more similar patients. For example, the initial parameters can be input by a medical professional and chosen based on parameters used for similar patients (e.g., age, sex, size, weight, severity of OSA, etc.).

The nerve stimulator 12, implanted in the patient at a predefined location, can receive the initial parameters and set operations according to the initial parameters. The nerve stimulator 12 can deliver a stimulation according to the initial parameters. The one or more sensors 14 can record from a patient during and/or after such a stimulation by the nerve stimulator 12. The one or more sensors 14 can be polysomnography sensors (e.g., electroencephalogram sensors, electrooculography sensors, electromyogram sensors, electrocardiogram sensors, respiratory inductance plethysmography sensors, or nasal airflow sensors), esophageal manometry sensors, and/or pharyngeal manometry sensors.

The computing device 16 can receive data from the one or more sensors 14 and analyze the data. During the analysis of the data, the computing device 16 can recognize decreases in airflow and/or pharyngeal obstruction via analysis of the sensor data. The computing device 16 can also recognize signs of arousal from sleep based on the analysis of the sensor data. Based on the analysis, the computing device 16 can adjust the parameters and transmit the adjusted parameter to the cranial or peripheral nerve stimulator 12. As an example, at least a portion of the adjusted parameters can be a static value. As another example, at least a portion of the adjusted parameters can be variable—such as, between a range of stimulation settings from which the patient can manually select a preferred setting at a later time, a range of stimulation parameters that can be used in a closed-loop fashion by an implanted pulse generator for the nerve stimulator according to pre-specified criteria after programming such as in response to certain biometric signal data, or the like. When more than one neural stimulator is used, the parameter for one nerve stimulator can depend on the parameters for the other nerve stimulator, for example. In some instances, the medical professional would have the ability to override the computing device 16.

The computing device 16 can perform a titration of the nerve stimulator 12 (or plurality of nerve stimulators) based on inputs from one or more sensors 14. The inputs from the one or more sensors 14 can indicate that the patient is experiencing collapse of the tongue or collapse of the lateral pharyngeal sidewalls or other airway obstruction. The one or more sensors 14 can also indicate whether the patient is waking. The titration can be used to find parameters in which airway obstruction (e.g., via collapse of the tongue, collapse of the lateral pharyngeal sidewalls, and/or other airway structures) does not occur and the patient does not awaken. The titration can be for one nerve stimulator 12, but can occur across multiple nerve stimulators, in some instances.

For example, the computing device 16 can receive inputs containing sensor data from multiple sensors 14. The computing device can construct a pressure pattern based on at least a portion of the sensor data. By analyzing the pressure pattern, the computer can match the pressure pattern to template patterns (e.g., one corresponding to no collapse and one corresponding to collapse) to determine whether the patient's tongue has collapsed or is collapsing into the airway. When the tongue is determined to be collapsing or to have collapsed, the parameter can be readjusted by the computing device 16 because the stimulation is subtherapeutic and sent to the nerve stimulator 12.

In situations where the tongue is determined not to be collapsing or to have collapsed, the computing device 16 can perform further analysis of the sensor data. For example the position, amplitude, and frequency of at least a portion of the sensor data can be determined. If at least one of the amplitude and frequency is higher than a baseline, the patient can be determined as experiencing collapse of other pharyngeal structures such as the pharyngeal sidewalls, the soft palate, or the epiglottis, and the computing device 16 can readjust the parameters because the stimulation is subtherapeutic, and the new parameters are sent to the nerve stimulator 12. However, if the position, amplitude, or frequency are less than or equal to the baseline, the patient can be determined as not experiencing pharyngeal sidewall, soft palate, or epiglottic collapse.

After the stimulation is delivered, the computing device 16 can also determine if the stimulation has caused the patient to arouse based on at least a portion of the sensor data. A stimulation that causes arousal of the patient can be determined to be a supratherapeutic stimulation and the computing device 16 can reduce one or more parameters of the stimulation and the reduced one or more parameters to the nerve stimulator 12.

Figure 2:
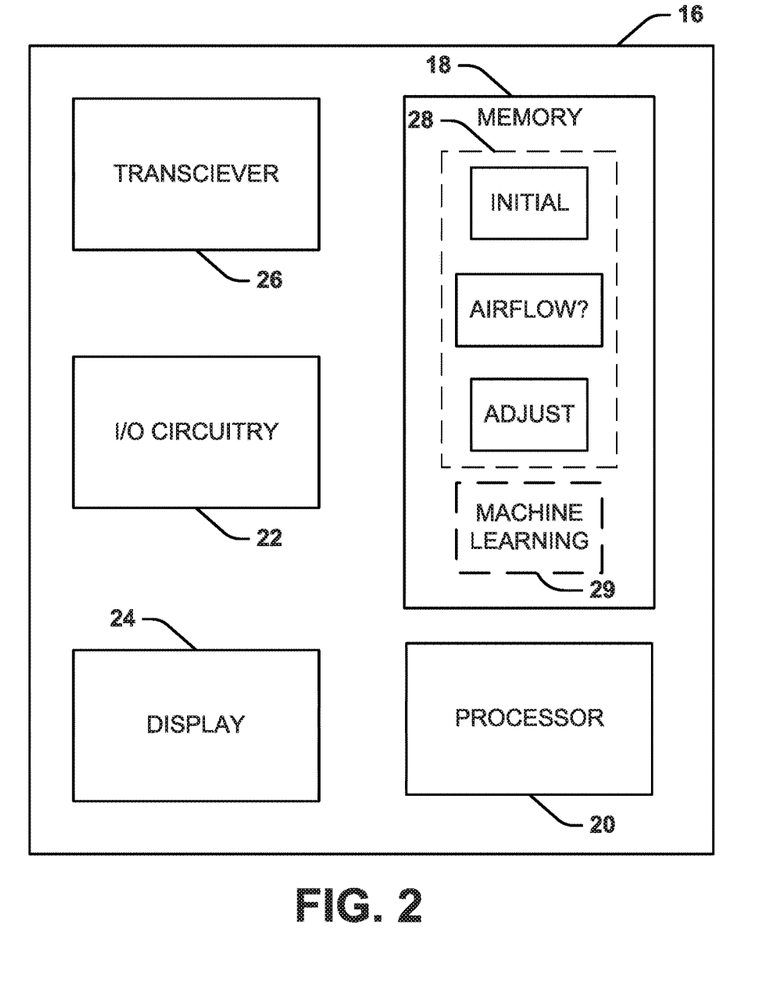
FIG. 2 is a schematic diagram of the computing device used by the system of FIG. 1.

The computing device 16 as shown in FIG. 2 can include memory 18 (which is a non-transitory memory device), a processor 20. I/O circuitry 22, a display 24, and a transceiver 26 (e.g., a wireless transceiver configured to facilitate short range transmission). The processor 20 can access the memory 18 and execute instructions 28 stored in the memory 18.

The instructions 28 can include an explicit predetermined algorithm for adjusting the parameters of a nerve stimulator titration, which, in some instances, may employ machine learning 29. The instructions 28 can include setting an initial parameter for stimulation by the nerve stimulator. This initial parameter can be based on an input from the I/O circuitry 22 and/or based on an initial parameter chosen based on properties of the patient. The instructions 28 can also include analyzing sensor data to assess airflow, for example, by sensing negative pressure changes within the airway, increased thoracic or abdominal respiratory effort, significant changes in oral or nasal airflow sensor data, or the like. The analysis can reveal whether the stimulation with the initial parameter provides a therapeutic stimulation, a subtherapeutic stimulation, or a supratherapeutic stimulation. In the event of a subtherapeutic stimulation or a supratherapeutic stimulation, the initial parameter is adjusted to an adjusted parameter. This process can continue until a therapeutic stimulation is reached.

The analyzing can also be aided by machine learning 29. The machine learning 29 can include an algorithm that can be trained to recognize supratherapeutic stimulations and/or subtherapeutic stimulations. The machine learning 29 can allow active titration of the nerve stimulator 12. For example, the machine learning 29 can employ one or more machine learning algorithms, such as: Decision tree learning, Association rule learning, Artificial neural networks, Deep learning, Inductive logic programming, Support vector machines, Clustering, Bayesian networks, Reinforcement learning, Representation learning, Similarity and metric learning, Sparse dictionary learning, Genetic algorithms, Rule-based machine learning, Learning classifier systems, Feature selection, or the like. The machine learning 29 can be trained so that each decision regarding the subtherapeutic stimulation or supratherapeutic stimulation can lead to a more accurate adjusted parameter.

IV. Methods

Figure 3:
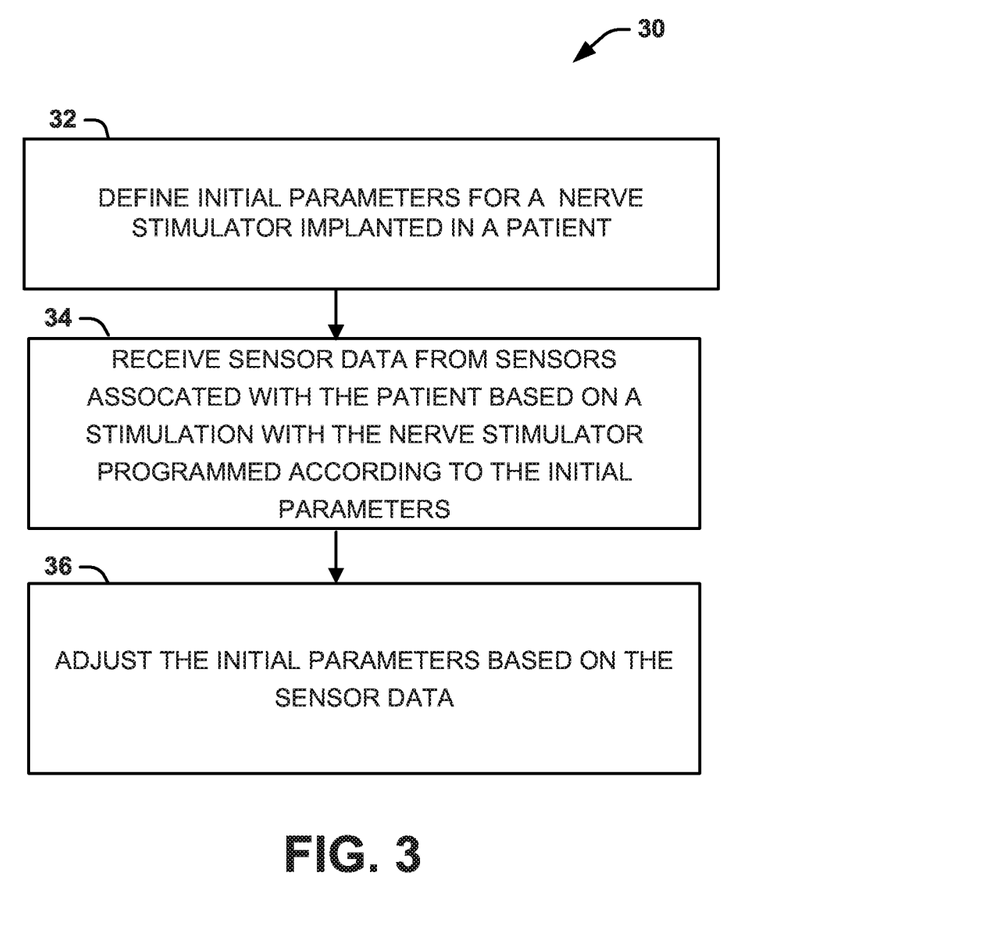
FIG. 3 is a process flow diagram illustrating a method for adjusting parameters of a nerve stimulator according to another aspect of the present disclosure.
Figure 4:
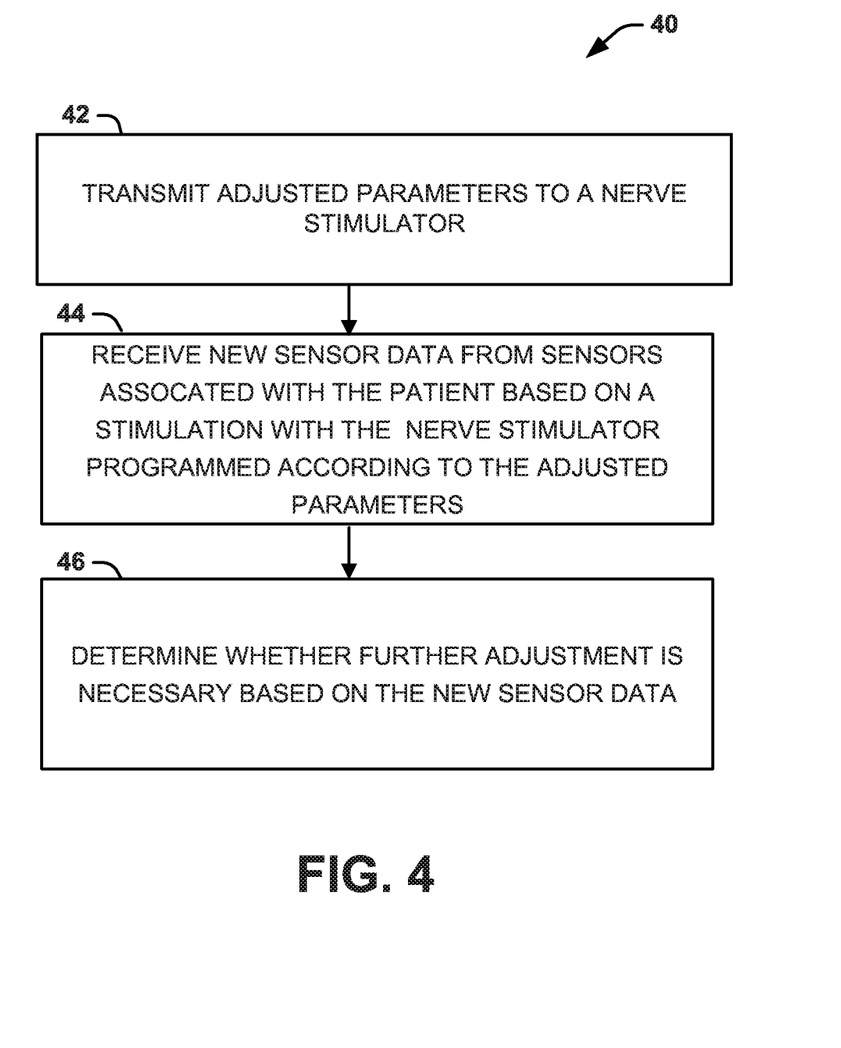
FIG. 4 is a process flow diagram illustrating a method for determining whether a nerve stimulator requires a further adjustment of parameters after the method of FIG. 3.
Figure 5:
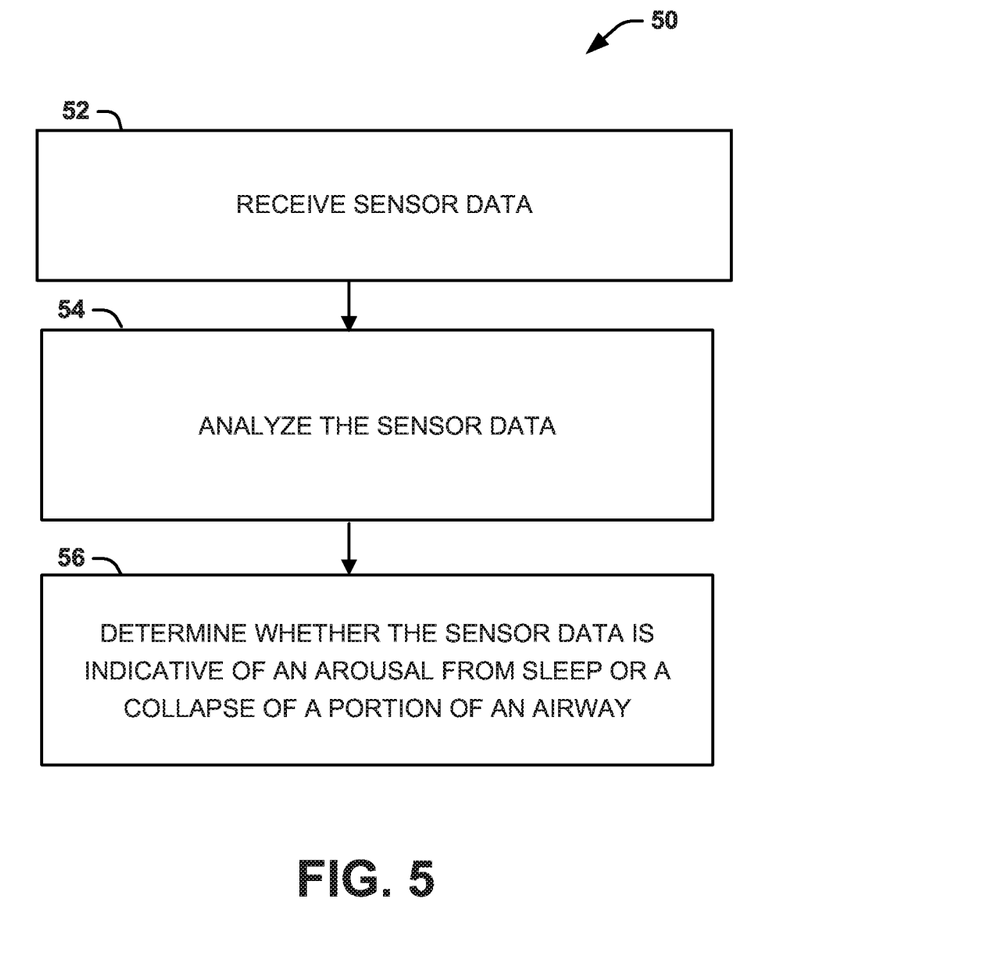
FIG. 5 is a process flow diagram illustrating a method for determining whether the patient is suffering from consequences necessitating a further adjustment of parameters after the method of FIG. 3.

Another aspect of the present disclosure can include methods 30-50 (FIGS. 3-5) for active titration of one or more nerve stimulators used to treat obstructive sleep apnea in real time as a collapse of the airway is occurring. Although a single nerve stimulator is described as being adjusted, it will be understood that the methods 30-50 can be used to set parameters for multiple stimulators in concert. FIG. 3 shows a method 30 for adjusting parameters of a nerve stimulator. FIG. 4 shows a method 40 for determining whether a nerve stimulator requires a further adjustment of parameters after the method of FIG. 3. FIG. 5 shows a method 50 for determining whether the patient is suffering from consequences such as decrease in airflow, blood oxygen desaturation, neurological arousals, or the like, necessitating a further adjustment of parameters after the method of FIG. 3. The methods 30-50 can be executed using the closed loop system 10 shown in FIG. 1 and described above.

The methods 30-50 are illustrated as process flow diagrams with flowchart illustrations. For purposes of simplicity, the methods 30-50 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 30-50. Additionally, one or more steps of the methods 30-50 can be stored on one or more non-transitory memory devices (e.g., memory 18 of FIG. 2) and executed using a hardware processor (e.g., processor 20 of FIG. 2) to perform operations associated with the one or more steps.

Referring now to FIG. 3, illustrated is a method 30 for adjusting parameters of one or more nerve stimulators after implantation into a patient. Although adjusting a single nerve stimulator is described, it will be understood that a plurality of nerve stimulators can be adjusted in concert according to the following method. The method 30 shows an execution of the feedback loop system 10 of FIG. 1 for the first time after implantation of a nerve stimulator. As an example, the nerve stimulator can be a hypoglossal nerve stimulator (HNS) that can provide stimulation that prevents airway closure during sleep characteristic of obstructive sleep apnea (OSA), an ansa cervicalis stimulator, or a combination thereof. The nerve stimulators can be unilateral stimulators of different nerves, bilateral stimulators of nerves of like kind, or a combination thereof.

At Step 32, initial parameters for a nerve stimulator (e.g., nerve stimulator 12 of FIG. 1) implanted within a patient (or to be implanted within the patient) can be defined (e.g. by computing device 16 of FIG. 1). The initial parameters can be determined based on a standard for similar patients based on pre-implantation testing. The initial parameters can be sent from the computing device to the nerve stimulator, which can implement the initial parameters. The computing device can communicate the parameters by a direct wired connection to the stimulation generator, or according to a wireless protocol, such as a short-range wireless protocol like Bluetooth or Bluetooth Low Energy.

The patient can receive stimulation with the nerve stimulator according to the initial parameters. At Step 34, sensor data can be received (by computing device 16 of FIG. 1) from one or more sensors (e.g., sensor(s) 14 of FIG. 1, including polysomnography sensors (e.g., electroencephalogram sensors, electrooculography sensors, electromyogram sensors, electrocardiogram sensors, respiratory inductance plethysmography sensors, or nasal airflow sensors), esophageal manometry sensors, and/or pharyngeal manometry sensors) associated with the patient. The sensor data can be recorded in response to a stimulation being delivered by the nerve stimulator (e.g., nerve stimulator 12 of FIG. 1) programmed according to the initial parameters. The sensor data can be polysomnography data (e.g., electroencephalogram data, electrooculography data, electromyogram data, electrocardiogram data, respiratory inductance plethysmography data, or nasal airflow data), esophageal manometry data, and/or pharyngeal manometry data. In any event, the computing device can recognize decreases in airflow and/or pharyngeal obstruction, blood oxygen desaturation, or neurologic arousal via analysis of the sensor data.

At Step 36, the initial parameters can be adjusted (e.g., by computing device 16 of FIG. 1) based on the sensor data. The adjustment can be based on application of a trained machine learning algorithm based on the sensor data. As an example, the sensor data can indicate that the stimulation aroused the patient from sleep (the stimulation was supratherapeutic), caused a portion of the patient's airway to collapse (the stimulation was subtherapeutic), or provided an appropriate stimulation (the stimulation was therapeutic). The adjusted parameters can be sent to the nerve stimulator for implementation. The adjusted parameters can be transmitted wirelessly (e.g., according to a short-range protocol like Bluetooth or Bluetooth Low Energy). Alternatively, the adjusted parameters can be transmitted over a wired connection. As another alternative, the adjusted parameters can be transmitted over a wired and wireless connection. As an example, at least a portion of the adjusted parameters can be a static value. As another example, at least a portion of the adjusted parameters can be variable—such as, between a range of stimulation settings from which the patient can manually select a preferred setting at a later time, a range of stimulation parameters that can be used in a closed-loop fashion by an implanted pulse generator for the nerve stimulator according to pre-specified criteria after programming such as in response to certain biometric signal data, or the like. A medical professional, in some instances, may have the ability to override any decision by the computing device.

After the initial parameters are adjusted, the feedback loop continues in FIG. 4, which shows a method 40 for determining whether a nerve stimulator requires a further adjustment of parameters. The method 40 can provide active titration for the stimulator device responsive to data recorded by one or more sensors during or after each stimulation.

At Step 42, adjusted parameters are transmitted (e.g., from computing device 16 of FIG. 1) to a nerve stimulator (e.g., nerve stimulator 12 of FIG. 1). The transmission can be a wireless transmission, such as a short range wireless transmission, like Bluetooth or Bluetooth Low Energy. At Step 44, new sensor data is received (e.g., by computing device 16 of FIG. 1) from sensors (e.g., sensor(s) 14 of FIG. 1) associated with the patient based on a stimulation with the nerve stimulator (e.g., nerve stimulator 12 of FIG. 1) programmed according to the adjusted parameters. The sensor data can be polysomnography data (e.g., electroencephalogram data, electrooculography data, electromyogram data, electrocardiogram data, respiratory inductance plethysmography data, or nasal airflow data), esophageal manometry data, and/or pharyngeal manometry data. In any event, the computing device can recognize decreases in airflow and/or pharyngeal obstruction via analysis of the sensor data. At Step 46, a determination is made (e.g., by computing device 16 of FIG. 1) as to whether further adjustment is necessary based on the new sensor data. The machine learning algorithm can be trained to recognize further evidences of arousal or collapse based on the adjusted parameters and can adjust to more favorable parameters due to the training. A medical professional, in some instances, may have the ability to override any decision by the computing device.

Referring now to FIG. 5, illustrated is a method 50 for determining whether the patient is suffering from consequences necessitating a further adjustment of parameters. At step 52, sensor data (e.g., from sensors 14 of FIG. 1) can be received (e.g., by computing device 16 of FIG. 1). The sensor data can correspond to recordings taken during and/or after stimulation by a nerve stimulator. At Step 54, the sensor data can be analyzed (e.g., by computing device 16 of FIG. 1). In some instances, the computing device can execute a trained machine learning algorithm to analyze the sensor data. At Step 56, a determination of whether the sensor data is indicative of an arousal from sleep (supratherapeutic) or a collapse of a portion of the airway (subtherapeutic) can be determined. If there is no detection of an arousal or a collapse, the sensor data can be deemed to be indicative of a therapeutic stimulation.

From the above description, those skilled in the art will perceive improvements, changes and modifications. Such improvements, changes and modifications are within the skill of one in the art and are intended to be covered by the appended claims.

The following is claimed:

1. A system for determining stimulation parameters for at least two nerve stimulators already implanted or positioned on a patient to improve obstructive sleep apnea comprising:
 a non-transitory memory storing instructions; and
 a processor to execute the instructions to:
  receive sensor data comprising at least pharyngeal manometry data from a pharyngeal manometry sensor that is external to the at least two nerve stimulators, the pharyngeal manometry sensor data indicating the location in the pharynx where pressure has changed; and
  define the stimulation parameters for programming each of the at least two nerve stimulators based on the location in the pharynx where pressure has changed as determined by the pharyngeal manometry sensor data, to improve the patient's obstructive sleep apnea, the at least two nerve stimulators configured to stimulate different cranial or peripheral nerves.

2. The system of claim 1, wherein the sensor data is indicative of an arousal from sleep of the patient.

3. The system of claim 1, wherein the sensor data further comprises polysomnography data.

4. The system of claim 3, wherein the polysomnography data includes electroencephalogram data, electrooculography data, electromyogram data, electrocardiogram data, respiratory inductance plethysmography data, nasal airflow data, blood oxygen desaturation or combinations thereof.

5. The system of claim 1, wherein the sensor data is indicative of a decrease in airflow due to pharyngeal obstruction.

6. The system of claim 1, wherein defining the stimulation parameters comprises adjusting the stimulation parameters based on the sensor data and actively titrating the at least two nerve stimulators by transmitting the adjusted stimulation parameters to the at least two nerve stimulators.

7. The system of claim 6, wherein the adjusted stimulation parameters are transmitted by wireless connection.

8. The system of claim 7, wherein the wireless connection is a short-range wireless connection.

9. The system of claim 1, wherein the stimulation parameters are adjusted by applying a trained machine learning algorithm to the sensor data.

10. A method for improving sleep apnea by at least two nerve stimulators configured to stimulate at least two cranial or peripheral nerves already implanted or positioned on a patient comprising:
 receiving, by a system comprising a processor, sensor data from at least a pharyngeal manometry sensor that is external to the at least two nerve stimulators, the pharyngeal manometry sensor data indicating the location in the pharynx where pressure has changed;
 defining system stimulation parameters for programming each of the at least two nerve stimulators based on the location in the pharynx where pressure has changed as determined by the pharyngeal manometry sensor data; and
 applying the stimulation parameters to the at least two nerve stimulators to improve the patient's obstructive sleep apnea.

11. The method of claim 10, wherein the defining further comprises adjusting the stimulation parameters applied to the at least two nerve stimulators to titrate the at least two nerve stimulators.

12. The method of claim 11, wherein the adjusted stimulation parameters are received by the at least two nerve stimulators according to a short-range wireless connection and/or a wired connection.

13. The method of claim 11, wherein the at least two nerve stimulators is titrated responsive to the sensor data.

14. The method of claim 10, wherein the defining further comprises applying a trained machine learning algorithm to the sensor data.

15. The method of claim 10, wherein the sensor data is indicative of an arousal from sleep of the patient.

16. The method of claim 10, wherein the sensor data further comprises polysomnography data.

17. The method of claim 16, wherein the polysomnography data includes electroencephalogram data, electrooculography data, electromyogram data, electrocardiogram data, respiratory inductance plethysmography data, nasal airflow data, blood oxygen desaturation or combinations thereof.

18. The method of claim 10, wherein defining further comprises adjusting the stimulation parameters of each of the at least two nerve stimulators.

19. The method of claim 18, wherein the adjusting further comprises adjusting the stimulation parameters of one of the at least two nerve stimulators based on adjusted stimulation parameters of another of the at least two nerve stimulators.

20. The system of claim 1, wherein the sensor data comprises esophageal manometry data and the sensor is an esophageal sensor.

21. The system of claim 1, wherein the sensor data comprises polysomnography data, esophageal manometry data, in addition to the pharyngeal manometry data.

22. A system for determining stimulation parameters for at least two nerve stimulators configured to stimulate at least two cranial or peripheral nerves already implanted or positioned on a patient to improve obstructive sleep apnea comprising:
a non-transitory memory storing instructions; and
a processor to execute the instructions to:
receive sensor data comprising at least an esophageal manometry data from an esophageal manometry sensor that is external to the at least two nerve stimulators, the sensor data at least indicative of a decrease in airflow due to pharyngeal obstruction; and
define the stimulation parameters for programming the at least two nerve stimulators based on the esophageal manometry data to improve the patient's obstructive sleep apnea, the at least two nerve stimulators configured to stimulate different cranial or peripheral nerves.

* * * * *